United States Patent [19]

Martineau et al.

[11] Patent Number: 5,175,095
[45] Date of Patent: Dec. 29, 1992

[54] OVARY-TISSUE TRANSCRIPTIONAL FACTORS

[75] Inventors: Belinda M. Martineau, Davis; Catherine M. Houck, Vacaville, both of Calif.

[73] Assignee: Calgene, Inc., Davis, Calif.

[21] Appl. No.: 554,195

[22] Filed: Jul. 17, 1990

Related U.S. Application Data

[63] Continuation-in-part of Ser. No. 382,518, Jul. 19, 1989, abandoned.

[51] Int. Cl.[5] .................... C12P 21/00; C12P 21/04; C12N 15/00; C12N 5/14; C12N 15/11; A01H 1/04
[52] U.S. Cl. .................... 435/69.1; 435/70.1; 435/172.3; 435/240.4; 435/320.1; 800/205; 800/DIG. 44; 536/27; 935/35; 935/36; 935/64; 935/67
[58] Field of Search ................ 435/69.1, 172.3, 320.1, 435/240.4, 70.1; 800/205, DIG. 44; 536/27; 935/35, 36, 64, 67

[56] References Cited

U.S. PATENT DOCUMENTS

4,801,540 1/1989 Hiatt et al. .................... 435/172.3
4,943,674 7/1990 Houck et al. .................... 800/205

FOREIGN PATENT DOCUMENTS

88/09334 12/1988 PCT Int'l Appl. .
89/12386 12/1989 PCT Int'l Appl. .

OTHER PUBLICATIONS

Murai et al. 1983. Science 222:476-482.
Larkins et al. 1985. J. Cell. Biochem. Suppl. 9C: 264.
Barker et al. 1983. Plant Mol. Biol. 2:335-350.
McCormick et al. 1987. Tomato Biotechnol., Nevins et al., eds., Alan R. Liss, Inc.: New York, pp. 255-265.
Piechulla et al. 1986. Plant Mol. Biol. 7:367-376.
Grierson et al. 1986, Nucleic Acids Res. 14:8595-8603.
McCormick et al. 1986. Plant Cell. Rep. 5:81-84.
Bird, C. R. et al., "The tomato polygalaturonase gene and ripening-specific expression in transgenic plants" *Plant Molecular Biology* 11: 651-662 (1988).
Hiatt, W. R. et al., "Expression of selected genes during tomato fruit maturation and ripening" *J. Cell Biochem.* Supp. O: 148 (1988).
Benfey, P. N. and Chua, N., "Regulated Genes in Transgenic Plants" *Science* 244:174-181 (1989).
An, G. et al., "Organ-specific and developmental regulation of the nopaline synthase promoter in transgenic tobacco plants" *Chemical Abstracts* 110:122 (1989).
Martineau, B. and Houck, C. M., "Wound-Inducible Expression of a Gene From Tomato" *J. of Cellular Biochemistry* 14E:306 (1990).
Hass, G. M. and Hermodson, M. A., "Amino Acid Sequence of a Carboxypeptidase Inhibitor from Tomato Fruit" *Biochemistry* 20:2256-2260 (1981).
Gasser, C. S. et al., "Analysis of Floral Specific Genes," *J. Cellular Biochem.* 12C:137 (1988).
Goldberg, R. B., "Plants: Novel Development Processes" *Science* 240:1460-1467 (1988).

*Primary Examiner*—David T. Fox
*Attorney, Agent, or Firm*—Barbara Rae-Venter

[57] ABSTRACT

Novel DNA constructs are provided which may be used as molecular probes or inserted into a plant host to provide for modification of transcription of a DNA sequence of interest in ovary tissue, particularly in very early fruit development. The DNA constructs comprise a transcriptional initiation regulatory region associated with gene expression in ovary tissue from immediately prior to anthesis through flower senescence.

8 Claims, 9 Drawing Sheets

```
1   AAAAAAACAAAAACATTTCTAATCTTTTTCACTCATTCCATGGCTCGTTCCATTTTCTTCATGGCATTT    69
    TTTTTTTGTTTTTGTAAAGATTAGAAAAAGTGAGTAAGGTACCGAGCAAGGTAAAAGAAGTACCGTAAA
    LysLysThrLysThrPheLeuIlePhePheThrHisSerMETAlaArgSerIlePhePheMETAlaPhe

70  TTGGTCTTGGCAATGATGCTCTTTGTTACCTATGAGGTAGAAGCTCAGCAAATTTGCAAAGCACCAAGC    138
    AACCAGAACCGTTACTACGAGAAACAATGGATACTCCATCTTCGAGTCGTTTAAACGTTTCGTGGTTCG
    LeuValLeuAlaMETMETLeuPheVALThrTyrGluValGluAlaGlnGlnIleCysLysAlaProSer

139 CAAACTTTCCCAGGATTATGTTTTATGGACTCATCATGTAGAAAATATTGTATCAAAGAGAAATTTACT   207
    GTTTGAAAGGGTCCTAATACAAAATACCTGAGTAGTACATCTTTTATAACATAGTTTCTCTTTAAATGA
    GlnThrPheProGlyLeuCysPheMETAspSerSerCysArgLysTyrCysIleLysGluLysPheThr

208 GGTGGACATTGTAGCAAACTCCAAAGGAAGTGTCTATGCACTAAGCCATGTGTATTTGACAAATCTCA    276
    CCACCTGTAACATCGTTTGAGGTTTCCTTCACAGATACGTGATTCGGTACACATAAACTGTTTTAGAGT
    GlyGlyHisCysSerLysLeuGlnArgLysCysLeuCysThrLysProCysValPheAspLysIleSer

277 AGTGAAGTTAAAGCAACTTTGGGTGAGGAAGCAAAAACTCTAAGTGAAGTTGTGCTTGAAGAAGAGATT   345
    TCACTTCAATTTCGTTGAAACCCACTCCTTCGTTTTTGAGATTCACTTCAACACGAACTTCTTCTCTAA
    SerGluValLysAlaThrLeuGlyGluGluAlaLysThrLeuSerGluValValLeuGluGluIle

346 ATGATGGAGTAATAATTAAGTGAGGTTAAATAAGGATTTTGAGTGTCAAAAAAACAAAATTAATAAAG    414
    TACTACCTCATTATTAATTCACTCCAATTTATTCCTAAAACTCACAGTTTTTTTGTTTTAATTATTTC
    METMETGlu . . LeuSerGluValLys . GlyPhe . ValSerLysLysThrLysLeuIleLys

415 TGTTGCCTTTTCTTATTAGGGTAGCTTGTGATGTTGTGTTAGTATTGGCCTATAGTAGCCATTTGACAC   483
    ACAACGGAAAAGAATAATCCCATCGAACACTACAACACAATCATAACCGGATATCATCGGTAAACTGTG
    CysCysLeuPheLeuLeuGly . LeuValMETLeuCys . TyrTrpProIleValAlaIle . His

484 ATTAAATAAGTTTGTGACACATCATTAATCCTTATGTATGTATGTTTAATGAAAAATGATCGACTACG   552
    TAATTTATTCAAACACTGTGTAGTAATTAGGAATACATACATACAAAATTACTTTTTACTAGCTGATGC
    IleLys . ValCysAspThrSerLeuIleLeuMETTyrValCysPheAsnGluLys . SerThrThr

553 ATCTTTAATTTT   564
    TAGAAATTAAAA
    IlePheAsnPhe
```

1   AAAAAAACAAAACATTTCTAATCTTTTCACTCATTCCATGGCTCGTTCCATTTTCTTCATGGCATTT                69
    TTTTTTGTTTTGTAAAGATTAGAAAAAGTGAGTAAGTACCGAGCAAGTAAAAGAAGTACCGTAAA
    LysLysThrLysThrPheLeuIlePhePheThrHisSerMETAlaArgSerIlePhePheMETAlaPhe

70  TTGGTCTTGGCAATGATGCTCTTTGTTACCTATGAGGTAGAAGCTCAGCAAATTGCAAAGCACCAAGC            138
    AACCAGAACCGTTACTACGAGAAACAATGGATACTCCATCTTCGAGTCGTTTAAACGTTCGTGTTCG
    LeuValLeuAlaMETMETLeuPheVALThrTyrGluValGluAlaGlnGlnIleCysLysValAlaProSer

139 CAAACTTTCCCAGGATTATGTTTTATGGACTCATCATGTAGAAAATATTGTATCAAAGAGAAATTTACT          207
    GTTTGAAAGGGTCCTAATACAAAATACCTGAGTAGTACATCTTTTATAACATAGTTTCTCTTTAAATGA
    GlnThrPheProGlyLeuCysPheMETAspSerSerCysArgLysTyrCysIleLysGluLysPheThr

208 GGTGGACATTGTAGCAAACTCCAAAGGAAGTGTCTATGCACTAAGCCATGTGTATTTGACAAATCTCA           276
    CCACCTGTAACATCGTTTGAGGTTTCCTTCACAGATACGTGATTCGGTACACATAAACTGTTTAGAGT
    GlyGlyHisCysSerLysLeuGlnArgLysCysLeuCysThrLysProCysValPheAspLysIleSer

277 AGTGAAGTAAAGCAACTTTGGGTGAGGAAGCAAAAACTCTAAGTGAAGTTGTGCTTGAAGAAGAGATT          345
    TCACTTCAATTTCGTTGAAACCCACTCCTTCGTTTTGAGATTCACTTCAACACGAACTTCTTCTCTAA
    SerGluValLysAlaThrLeuGlyGluAlaLysThrLeuSerGluValValLeuGluGluGluIle

346 ATGATGGAGTAATAATTAAGTGAGGTTAAATAAGGATTTGAGTGTCAAAAAAAACAAATTAATAAAG            414
    TACTACCTCATTATTAATTCACTCCAATTTATTCCTAAACTCACAGTTTTTTTTGTTTAATTATTTC
    METMETGlu . . LeuSerGluValLys . GlyPhe .  ValSerLysLysThrLysLeuIleLys

*FIGURE 1A*

415 TGTTGCCTTTTCTTATTAGGGTAGCTTGTGTAGTGTTGTAGTATTGGCCTATAGTAGCCATTGACAC 483
    ACAACGGAAAAAGAATAATCCCATCGAACACTACAACACCAATCATAACCGGATATCATCGGTAAACTGTG
    CysLeuPheLeuLeuGly . LeuValMETLeuCys . TyrTrpProIleValAlaIle . His

484 ATTAAATAAGTTTGTGACACATCATTAATCCTTATGTATGTTTAATGAAAAATGATCGACTACG 552
    TAATTTATTCAAACACTGTGTAGTAATTAGGAATACATACATACAAAATTACTTTTACTAGCTGATGC
    IleLys . ValCysAspThrSerLeuIleLeuMETTyrValCysPheAsnGluLys . SerThrThr

553 ATCTTTAATTTT 564
    TAGAAATTAAAA
    IlePheAsnPhe

*FIGURE 1B*

```
   1  GCTCCACTACTCTCATCACTTTAGTTCATCAAGCCTTCTTTTATACCAA       49
  50  GGCATCAATCATCATTAGTTACACAAAGTAGATTAGGGTTTTTCAAGATTTA     98
  99  GGATTCAATAGCTTCATCATGCTTATTTTATCACAATTATATAATCACA       147
 148  TTCATACAAGCATACAATTAAGCATATAGAAGGGTTTACAATACTACCC       196
 197  AATACATATCATTCGCTATTAAGAGTTTACTACGAATAGCATAAACCAT       245
 246  AACCTACCTCCACCGAAGAATCGCGATCAAACAATCTACTTTCCCAAAG       294
 295  CTGCGTTCTTCTTCGTTTCTCTATTTTCTTGATCGTTCGTTTCTCCCTC       343
 344  TCTTTGTTCTTTCTATTTTCTTAAACCCTCTTCTTTCTTTTACCCTA         392
 393  ATTAGTATATAATTAAGTATAAAAGATGATAAAATACCCCATCTATTTG       441
 442  TTTGAAGGTTATCTCTTTTAGCCCCCCAAGTAATTATTAACATTA           490
 491  AACCACTAACTTTATAATTATAAGCAGGAATAGTCCAAAACGCCCCTTA       539
 540  AAATATTTAACAGAAATCCGACCCAGTCAGGGTCACGCAGCCTGTANCG       588
 589  GNNCACAAACTGTGACGGTCCGTCCTGCATGGCCGTCACAAAGTTCAGAG      637
 638  AGTTAATTTCTGTGGAAGATGTGTTACGAAGTTCAGAGAGTCGACGGTCC      686
 687  GTCCTGTCATTTCGTTACGAAGTTCAGAGTCGATTTCAGTACCCAAA         735
         EcoRI
 736  TTTCAGAATTCTAAGTGTTTGGAACGAGACCCCNCGGTCCGTCGTGCC         784
                                 BamHI  SalI
 785  CATGACGGTTCGTCGTGGATCCGTCGACTCAGCCAGTTTTCCAAAAT          833
 834  TAAAATCTGCTGCTCAAAACGACTAAACAGGTCGTTACAAAGTACTCAA       882
 883  TCAAATAAAAGAATAAATTCTTTTCCAAATACATATATTGTTTATAGG       931
 932  ACAGTGTTAACAGGGAAATGTAATCGTTGCCTCAATCGATTTTTTTT         980
                        BglII
 981  TGAAATTAAGATTGATTAGATCTTCTTTAAGATAACAATGTCTCAAAGA       1029
1030  TAAATTGAATGAATGAATTAGCTATATTATCATTTGAAAAGAAATTACT       1078
1079  AAAACAGATTGATAATAATAAAATAAATAATAAATGACTTTGCATCTAAAATA   1127
```

*FIGURE 2A*

| | | |
|---|---|---|
| 1128 | GCTAGAAAGCAGATTTTAAATAAAATACATATGATAAAAAAGATA | 1176 |
| 1177 | AATTAGAGTCATCCCATAAATTTCGCTTTAGCCCCCAATGTGTTAAG | 1225 |
| 1226 | TCGGCCCTGAAAATAGGAATGGTATTAAATATTTGTTTTGATTTCACA | 1274 |
| 1275 | CTTGATATTTGACATTCATATTAGAAAATAATTTATATTCGTGT | 1323 |
| 1324 | AGAGTGGTCTCACATTAATGGGTAAAATATTTCCACACAAAACTATTT | 1372 |
| 1373 | TACAATCATAGCTAGAATCTGAAATCTAATGTACTCCACCAATTAA | 1421 |
| 1422 | TTAAAGATGATTTTTGCTTAAATAAAAAATATGTCTATTGCCAAA | 1470 |
| 1471 | CTACTAATAGATGTACTCACAAAAAAAAATAAAATCAAGTGTA | 1519 |
| 1520 | TATACAATGATTCGGAAGGCCATTTTGAAATTTCATAAATGACCG | 1568 |
| 1569 | TTTTACCCGTTCACAATTGTGTTTCAGCATTTTTGTTTGTTTGTGGA | 1617 |
| | | HindIII |
| 1618 | TTTGGTTATGGAAGTTCAATAAAAAGTGTGGTTTATAAGCTTTGGAG | 1666 |
| 1667 | TTTGAAAGTTAAGTTGATTAAAAGTAGTTTTAGTGTGTCAATTGGAG | 1715 |
| 1716 | TTTCGTGTCTTGAAATAAATTTTATCACTTGCATTAGTTTCAAAATGTC | 1764 |
| 1765 | GAGTTGGTTAAGTAGAGAGTTTTTTCATTCGGAGTTTAGCCTTTGAATT | 1813 |
| 1814 | TAAAATGTTAAGCTGAAAAGTTTTATGAAATTTTTTGAGTTAATTT | 1862 |
| 1863 | TGATGCTTGAATTAAATTTTGAGAATTTTTTGAAATCTGGGATAAT | 1911 |
| 1912 | GTTAGGTCTTAGAGAAGTCTGGTTGTTTGAATTTCATAGCTCAAGAGATTAG | 1960 |
| 1961 | TTTTGACTTTTTAGGCATTTTGGTTTATTACGATTTTCACGGACTT | 2009 |
| 2010 | TCGAATTAAGGAGACTTCAAAATTCATATTTAATGGTTCGTGTTCGT | 2058 |
| 2059 | TAGTTTTAAAAATCGTGTCTTTATAAGGATTTATACTTAAAAAATAAA | 2107 |
| 2108 | ATAAAATAAAGTACTACTAACATGTAATTCTGTCATAAGATAAGGTTGT | 2156 |
| 2157 | ACATTAGGACTATTTGAATATTCATCAAAATAAAAAAAGTAGAGAT | 2205 |
| 2206 | GATAGTAATATAAATATTTATTTTTGATTTTACATTTGATATTTTAATA | 2254 |
| 2255 | CTAACAATATGACATAATAAAATTTGTATTCAGATTGTAAAATATTCCC | 2303 |
| 2304 | TAAAAAAAGATACTTTTACTGTGGCTCAAATTCAAAATTTTCTAAG | 2352 |

FIGURE 2B

```
2353  AAAAACTACTAATAATTGATTTCTAATTAAAATTTCGATATATATATAT  2401
2402  ATATATATATATATATCATAATATACTTCACCTACCTCAATTATTATTA  2450
2451  TTTTCTTTTTTTTTACTTCACATATTTTTGGSCSACCAATTTTTTTTT   2499
2500  TAACTTTTTTGGTCTTACTCTTATTTCACTCCCTATAAATAACTCCCAT  2548
2549  TGTGTGATATTTTTATTCACAACTCTAACTTACAATTACAATCTTTCTTATTATT  2597
                         NcoI

2598  AAAAAAAACAAAAACATTTCTAATCTTTTTCACTCATTCCATGGCTCGT  2646
2647  TCCATTTCTTCATGGCATTTTGGTCTTGGCAATGATGCTCTTTGTTA    2695
2696  CCTATGgtttgtcttcataatttattcctctaaaatcatcgcaataaaa  2744
2745  aaaaatgtaacgaagcagacatcagtaaaccgtttaaataaaccctaa   2793
2794  aaaaattgtgaattgatattacttgctatacgtttaacaactatgataa  2842
2843  aaaaccctaaaatatacttatttcgatttcgtctctctcatgttattc   2891
2892  taactatttttgtgtgtgaatgattgtagAGTAGAAGCTCAGCAAAT    2940
2941  TTGCAAAGCACCAAGCCAAACTTTCCCAGGATTATGTTTTATGGACTCA  2989
2990  TCATGTAGAAAATATTGTATCAAAGAGAAATTTACTGGTGGACATTGTA  3038
3039  GCAAACTCCAAAGGAAGTGTCTATGCACTAAGCCATGTATTTGACAA    3087
3088  AATCTCAAGTGAAGTTAAAGCAACTTTGGGTGAGGAAGCAAAAACTCTA  3136
3137  AGTGAAGTTGTGCTTGAAGAGAGATTATGATGGAGTAATAATTAAGTG   3185
3186  AGGTTAAATAAGGATTTTGAGTGTCAAAAAAACAAAATTAATAAAGTG   3234
3235  TTGCCTTTTCTTATTGACACATTAAATAAGTTTGTGACACATCATTAATCC  3283
3284  ATAGTAGCCATTTGACACATTAAATAAGTTTGTGACACATCATTAATCC  3332
3333  TTATGTATGTATGTTTTAATGAAAAATGATCGACTACGATCTTTAATTT  3381
3382  TATGTTTTACATTTAATTAATCACTTTCTGTTACGATTCATTTATCTAG  3430
3431  TTATGAATGAAATATAGAGTGATTGAAGTAAGGAGCTAGTCTTCAAAC   3479
3480  AAAGACGTACATATGTACAAAGTAGGTACTATTAAACTTCTTTTTTAT   3528
```

*FIGURE 2C*

| | | |
|---|---|---|
| 3529 | GATTCGATATATTCATATTTGATACTCAAATTAGAGTTAAATTCATATT | 3577 |
| 3578 | AATTTGTACGAGAGAATTTAAACTAATAAATAAAACTCCCTAATAAA | 3626 |
| | EcoRI | |
| 3627 | AGATTACTTTCATGATAGAATATATAATATATTGAATTCTTGTTGCTGA | 3675 |
| 3676 | ATTTATATTATGGTCATGCAAAACTTAGGAAAATAAAATGAAAGATAAA | 3724 |
| 3725 | TAATATGTGCTTGATGACAACTTTATGCCTGAATAATAATATAATAAT | 3773 |
| 3774 | TAATATAAAATGATGAATTAATAATACTTTATAATAAGTTTTTTCTTCA | 3822 |
| 3823 | TCATTTGAATCTATTGAATGGTATTAAACATTTTATTTTGATTTTACAT | 3871 |
| 3872 | TCGATATTTGATATTTATAATAGAAAATGATTAAATTTATATTCGTTTA | 3920 |
| 3921 | GAGAGGTCTCATATTAAAGGATAAAAATATTATCTAATAAAGTTACTTT | 3969 |
| 3970 | ACAATCATAGTTAAAATCTGAAATATTGTAATGTTGTAATGACCCGATAG | 4018 |
| 4019 | ATTATTTTTGGGAATTTTAAACTATTGCTTAACTTAAGTTAATTAATT | 4067 |
| 4068 | CATGAATAATTATAGATAATTGACTTAATCAATAGTTAATGATACAACT | 4116 |
| 4117 | ATATACTATTTGACCCTTATAATGTGTGTTAAATATTGGTCTTTAGTA | 4165 |
| 4167 | GCCATTTGACACACATTAAATCATATCAGTATTGCATAAATATTCATGAGCTAAAA | 4215 |
| 4216 | ATCAATTAGAAATCATATCAGTAAATAATTTCAATTCATCGATTTGCAAAAA | 4264 |
| 4265 | AAAATTGAAAAAAAAATTAAACAATTGCACAATCCATCAATTAGCATTAAG | 4313 |
| 4314 | TTATGCAGAAAATTAAACAATTGCACAATCCATCAATTAGCATTAAG | 4362 |
| | BamHI | |
| 4363 | TATTTAGCCCTCTCTTGGATCC | 4384 |

*FIGURE 2D* pZ70

1   ATTATTATTACCATGGCACAAAAATTTACTATCCTTTTCACCATTCTCCTTGTGGTTATTGCTGCTCAA    69
              METAlaGlnLysPheThrIleLeuPheThrIleLeuLeuValValIleAlaAlaGln
                       Mature Protein Start

70  GATGTGATGGCACAAGATGCAACTTCTGACGAAACTTTTTCAGCAATATGATCCAGTTTGTCACAAACCT   138
    AspValMETAlaGlnAspAlaThrLeuThrLysLeuPheGlnGlnTyrAspProValCysHisLysPro

139 TGCTCAACACAAGACGATTGTTCTGGTACGTTCTGTCAGGCCTGTTGGAGGTTCGCGGGACATGT       207
    CysSerThrGlnAspAspCysSerGlyThrPheCysGlnAlaCysTrpArgPheAlaGlyThrCys
                       Mature Protein End

208 GGGCCCTATGTTGGGGCGCCATGGCCATAGGCGTGTGATTACAATTCGTTGTTCTTCTTTTTCGACT    276
    GlyProTyrValGlyArgAlaMETAlaIleGlyVal

277 TTTTAATCCCAAGTGAATAAAGTCTAATTCGAAAAGAAGAAAAAGTATCTATGTCTGAGTTATATGT    345

346 TTTGTGGCTAATAAGAAATCGACTATGCTTGTTGATTTGATAAAAATTATGTCATTAGGGTGTGATATG  414

415 TAATCATCAAATTAAATAAAAATCATCGCATTGTGTGTG   453

*FIGURE 4*

OVARY-TISSUE TRANSCRIPTIONAL FACTORS

CROSS-REFERENCE TO RELATED APPLICATIONS

This application is a continuation-in-part of U.S. application Ser. No. 382,518, filed Jul. 19, 1989, now abandoned, which application is incorporated herein by reference.

INTRODUCTION

1. Technical Field

This invention relates to in vitro constructed DNA transcription or expression cassettes capable of directing ovary-tissue transcription in plants at a very early stage of fruit development. The invention is exemplified by promoters useful in ovary-tissue transcription of a gene of interest in a tomato plant.

2. Background

In general, genetic engineering techniques have been directed to modifying the phenotype of individual prokaryotic and eukaryotic cells, especially in culture. Plant cells have proven more intransigent than other eukaryotic cells, due not only to a lack of suitable vector systems but also as a result of the different goals involved. For many applications, it is desirable to be able to control gene expression at a particular stage in the growth of a plant or in a particular plant part. For this purpose, regulatory sequences are required which afford the desired initiation of transcription in the appropriate cell types and/or at the appropriate time in the plant's development without having serious detrimental effects on plant development and productivity. It is therefore of interest to be able to isolate sequences which can be used to provide the desired regulation of transcription in a plant cell during the growing cycle of the host plant. One aspect of this interest is the ability to change the phenotype of fruit, both succulent and dry fruit, so as to provide for improved edible and non-edible aspects of quality, including protein composition, storage, handling, cooking, organoleptic properties, freezing, nutritional value and the like. Fruit of larger size or having an increased percent of solids are further examples of desired modified phenotypes.

However, in order to effect desired phenotypic changes, transcription initiation regions capable of initiating transcription only in early fruit development are needed. For example, it would be desirable to induce additional cell divisions prior to the onset of pollination and to have these effects lessen, if not cease, before fruit enlargement, tissue maturation, or the like occur, so as to provide for increased solids in the mature tissue, or larger mature tissue, particularly fruit.

RELEVANT LITERATURE

A class of fruit-specific promoters expressed at or during anthesis through fruit development, at least until the beginning of ripening, is discussed in European Application 88.906296.4, the disclosure of which is hereby incorporated by reference. cDNA clones from tomato displaying differential expression during fruit development have been isolated and characterized (Mansson et al., *Mol. Gen. Genet.* (1985) 200:356-361: Slater et al., *Plant Mol. Biol.* (1985) 5:137-147). These studies have focused primarily on mRNAs which accumulate during fruit ripening. One of the proteins encoded by the ripening-specific cDNAs has been identified as polygalacturonase (Slater et al., *Plant Mol. Biol.* (1985) 5:137-147). A cDNA clone which encodes tomato polygalacturonase has been sequenced (Grierson et al., *Nucleic Acids Research* (1986) 14:8395-8603). Improvements in aspects of tomato fruit storage and handling through transcriptional manipulation of expression of the polygalacturonase gene have been reported (Sheehy et al., *Proc. Natl. Acad. Sci. USA* (1988) 85:8805-8809; Smith et al., *Nature* (1988) 334: 724-726). Mature plastid mRNA for psbA (one of the components of photosystem II) reaches its highest level late in fruit development, whereas after the onset of ripening, plastid mRNAs for other components of photosystem I and II decline to nondetectable levels in chromoplasts (Piechulla et al., *Plant Molec. Biol.* (1986) 7:367-376). Recently, cDNA clones representing genes apparently involved in tomato pollen (McCormick et al., *Tomato Biotechnology* (1987) Alan R. Liss, Inc., N.Y.) and pistils (Gasser et al., *Plant Cell* (1989), 1:15-24) interactions have also been isolated and characterized.

Other studies have focused on genes inducibly regulated, e.g. genes encoding serine proteinase inhibitors, which are expressed in response to wounding in tomato (Graham et al., *J. Biol. Chem.* (1985) 260:6555-6560: Graham et al., *J. Biol. Chem.* (1985) 260:6561-6554) and on mRNAs correlated with ethylene synthesis in ripening fruit and leaves after wounding (Smith et al., *Planta* (1986) 168: 94-100). Accumulation of a metallocarboxypeptidase inhibitor protein has been reported in leaves of wounded potato plants (Graham et al., *Voiochem & BioPhys-Res Comm.* (1981) 101:1164-1170).

Transformation of cultivated tomato is described by McCormick et al., *Plant Cell Reports* (1986) 5:81-89 and Fillatti et al., *Bio/Technology* (1987) 5:726-730.

SUMMARY OF THE INVENTION

Novel DNA constructs and methods for their use are described which are capable of directing transcription of a gene of interest in ovary tissue, particularly early in fruit development. Expression cassettes comprising a transcriptional and translational initiation region obtainable from a gene expressed in ovary tissue joined to a DNA sequence of interest other than the wild-type sequence, and a transcription termination region are also provided. Fruit having an altered phenotype may be obtained by transforming a host plant cell of interest with the DNA construct. The transformed cell is then used to generate a plant, which is then grown to produce fruit having the desired altered characteristics. Transcription of the message encoded by the DNA sequence of interest under the control of the promoter region functional in ovary cells will occur prior to, and during, the pollination stage of the fruit. Constructs and methods of the subject invention thus find use in modulation of endogenous fruit products, as well as production of exogenous products an in modifying the phenotype of fruit and fruit products. The constructs also find use as molecular probes.

DESCRIPTION OF THE DRAWINGS

FIGS. 1A through 1B shows the DNA sequence of cDNA clone pZ130. The sequences corresponding to the pZ7 cDNA clone are underlined.

FIGS. 2A through 2D shows the sequence of the region of the Calgene Lambda 140 genomic clone that overlaps with the pZ130 cDNA clone (this region is underlined) and a partial sequence of regions 5' and 3' to that region. The start of the pZ130 gene transcript is indicated by the underlined, boldfaced "A" at position 2567. An intron in the gene sequence is indicated by the lower case sequence from position 2702 through position 2921. Sites for common restriction enzymes are indicated.

The symbols in the sequence have the following meaning:

A=adenosine; C=cytosine; G=guanine; T=tyrosine or uracil; R=A or G; Y=C or T or U; M=C or A; K=T or U or G; W=T or U or A; S=C or G; N=either C, T, A G or U; B=not A; D=not C; H=not G; V=not T or U.

Figure 3:
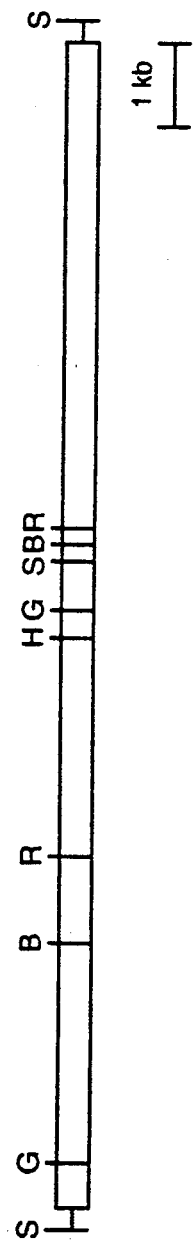

FIG. 3 shows a restriction map of Calgene Lambda 140. B: BamHi; G: BglII; HindIII; R: EcoRI;

FIG. 4 shows a complete DNA sequence of cDNA clone pZ70. The sequences corresponding to the pZ8 cDNA clone are underlined. The start and end of the mature protein encoded by the pZ70 gene are also indicated.

Figure 5:
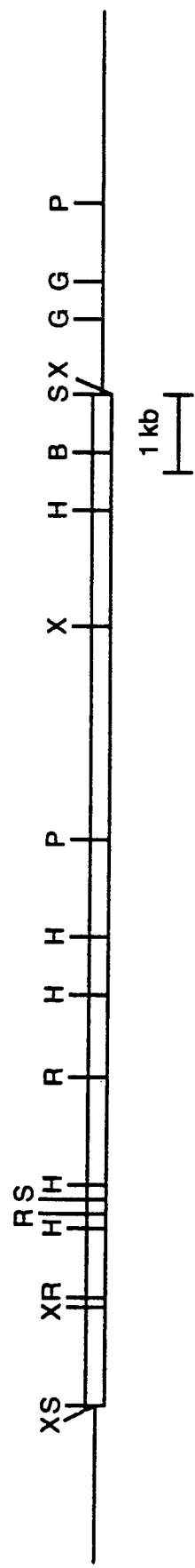

FIG. 5 shows a restriction map of Calgene Lambda 116. B: BamHI; G: BglII; H: HindIII; P: SphI; R: EcoRI; S: SalI; X: XbaI.

Figure 6:
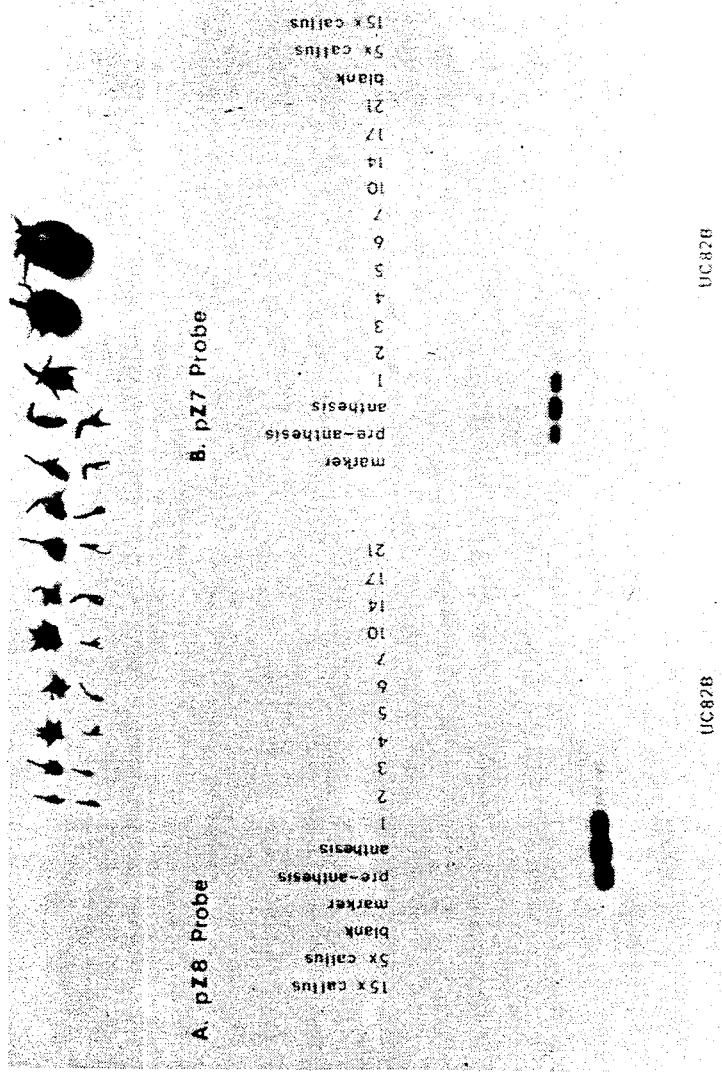

FIG. 6 shows the results of a Northern blot experiment illustrating a developmental time course of pZ7 and pZ8 RNA accumulation. The stages of UC82B fruit development (flowers and ovaries/fruit) are depicted above. Numbers 1 through 21 represent days post flower opening.

DETAILED DESCRIPTION OF THE INVENTION

In accordance with the subject invention, novel DNA constructs are provided which may be used as molecular probes or inserted into a plant host to provide for the preferential transcription of a gene of interest in ovary tissue as compared with other plant tissues. Of particular interest is the period of at least one to three days prior to anthesis through flower senescence.

The DNA constructs comprise transcriptional initiation regulatory regions associated with gene expression in ovary tissue. The regulatory regions are capable of directing transcription in ovaries from anthesis through flowering but direct little or no expression after the initial changes which occur at the time surrounding pollination and/or fertilization; transcription from these regulatory regions is not detectable at about three weeks after anthesis. Ovary-tissue transcript initiation regions of this invention are typically not readily detectable in other plant tissues. Nevertheless, ovary-specific transcription initiation regions may find special application.

Especially preferred are transcription initiation regions which are not found at other stages of fruit development. Transcription initiation regions capable of initiating transcription in other plant tissues and/or at other stages of ovary development, in addition to the foregoing, are acceptable insofar as such regions provide significant expression level in ovary tissue at the defined periods of interest and do not negatively interfere with the plant as a whole, and, in particular, with the development of fruit and/or related parts. Also of interest are ovary tissue promoters and/or promoter elements which are capable of directing transcription in specific ovary tissues such as outer pericarp tissue, inner core tissues, integuments, and the like.

A transcriptional cassette preferentially expressed in ovary tissue will include in the 5'→3' direction of transcription, an ovary tissue transcriptional initiation region and optionally a translational initiation region, a DNA sequence of interest, and a transcriptional and optionally translational termination region functional in a plant cell. When the cassette provides for the transcription and translation of a DNA sequence of interest it is considered an expression cassette. One or more introns may be also be present. For use in the subject invention, transcriptional initiation regions which are expressible in ovary tissue at or near maximal levels during the period of interest of this invention, generally the flowering period of plant reproductive cycles, are preferred. The transcription level should be sufficient to provide an amount of RNA capable of resulting in a modified fruit. The term "fruit" as used herein refers to the mature organ formed as the result of the development of the ovary wall of a flower and any other closely associated parts. See Weirer, T. E., 1, ed., *Botany A Introduction to Plant Biology* (6th ed.) (John Wiley & Sons, 1982); Tootill & Backmore, The Facts on File Dictionary of Botany (Market Home Books Ltd., 1984). By "modified fruit" is meant fruit having a detectably phenotypically different phenotype from an nontransformed plant of the same species, for example, one not having the transcriptional cassette in question in its genome.

With regard to the transcriptional and translational initiation region (also sometimes referred to as a "promoter,"), it preferably comprises a transcriptional initiation regulatory region and a translational initiation regulatory region of untranslated 5' sequences, "ribosome binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest It includes natural and synthetic sequences as well as sequences which may be a combination of synthetic and natural sequences.

Of particular interest are transcriptional initiation regions associated with genes expressed in ovary tissue and which are capable of directing transcription at least 24 hours prior to anthesis through flower senescence. The term "anthesis" refers herein to the period associated with flower opening and flowering. The term "flower senescence" refers herein to the period associated with flower death, including the loss of the (flower) petals, etc. Abercrombie, M., et al., *A Dictionary of Biology* (6th ed) (Penguin Books, 1973). Unopened flowers, or buds, are considered "pre-anthesis." Anthesis begins with the opening of the flower petals, which represents a sexually receptive portion of the reproductive cycle of the plant. Typically, flowering lasts approximately one week in the tested UCB82 tomato variety. It is preferred that the transcriptional initiation regions of this invention do not initiate transcription for a significant time or to a significant degree prior to plant flower budding Ideally, the level of transcription will be high for at least approximately one to three days and encompass the onset of anthesis ("perianthesis").

It further is desired that the transcriptional initiation regions of this invention show a decreased level of transcriptional activity within 1-3 days after the onset of anthesis which does not increase, and preferably decreases over time. Fertilization of a tomato embryo sac, to produce the zygote that forms the embryo plant, typically occurs 2-3 days after flower opening. This coincides with a decrease in the activity of a transcriptional initiation region of this invention. Thus, it is desired that the transcriptional activity of the promoter of this invention significantly decrease within about two days after the onset of anthesis. Transcriptional initiation regions of this intention will be capable of directing expression in ovary tissue at significant expression levels during the preferred periods described above.

In some embodiments, it will be desired to selectively regulate transcription in particular ovary tissue or tissues. When used in conjunction with a 5' untranslated sequence capable of initiating translation, expression in defined ovary tissue, including ovary integuments (also known a "ovule epidermal cells"), core or pericarp tissue, and the like, can direct a desired message encoded by a DNA sequence of interest in a particular tissue to more efficiently effect a desired phenotypic modification. For example, expression in ovary pericarp tissue, also known as the ovary wall and/or ovary core tissue, could result in useful modifications to the edible portions of many fruits, including true berries such as tomato, grape, blueberry, cranberry, currant, and eggplant; stone fruits (drupes), such as cherry, plum, apricot, peach, nectarine and avocado; and compound fruits (druplets), such as raspberry and blackberry. In hesperidium (oranges, citrus), such expression cassettes are expected to be expressed in the "juicy" portion of the fruit. In pepos, (such as watermelon, cantaloupe, honeydew, cucumber, and squash) the equivalent tissue is most likely the inner edible portions. In other fruits, such as legumes, the equivalent tissue is the seed pod.

The modification of analogous structures of non-edible fruit may also be of interest. Thus, of special interest are transcription initiation regions expressible in at least ovary outer pericarp tissue. For example, in cotton the analogous ovary structure is the burr of the cotton boll, in rapeseed it is the seed pod. In a like manner, regulating expression in ovary integuments and/or core tissue may result in useful modifications to the analogous fruit and related structures evolving therefrom, for example seed coat hairs, such as cotton.

To obtain a specifically derived transcriptional initiation region the following steps may be employed. Messenger RNA (mRNA) is isolated from tissue of the desired developmental stage, for example. This mRNA is then used to construct cDNA clones which correspond to the mRNA population both in terms of primary DNA sequence of the clones and in terms of abundance of different clones in the population. mRNA is also isolated from tissue of a different developmental stage in which the target gene should not be expressed (alternate tissue). Radioactive cDNA from the desired tissue and from the alternate tissue is used to screen duplicate copies of the cDNA clones. The preliminary screen allows classification of the cDNA clones as those which correspond to mRNAs which are abundant in both tissues; those which correspond to mRNAs which are not abundant in either tissue; those which correspond to mRNAs which are abundant in one tissue and relatively non-abundant in the other. Clones are then selected which correspond to mRNAs that are abundant only in the desired tissue and then further characterized.

Since the hybridization probe for the preliminary screen outlined above is total cDNA from a particular tissue, it hybridizes primarily to the most abundant sequences. In order to determine the actual level of expression, particularly in tissue where the mRNA is not as abundant, the cloned sequence is used as a hybridization probe to the total mRNA population(s) of the desired tissue(s) and various undesired tissue(s). This is most commonly done as a Northern blot which gives information about both the relative abundance of the mRNA in particular tissues and the size of the mRNA transcript.

It is important to know whether the abundance of the mRNA is due to transcription from a single gene or whether it is the product of transcription from a family of genes. This can be determined by probing a genomic Southern blot with the cDNA clone. Total genomic DNA is digested with a variety of restriction enzymes and hybridized with the radioactive cDNA clone. From the pattern and intensity of the hybridization, one can distinguish between the possibilities that the mRNA is encoded by one or two genes or a large family of related genes. It can be difficult to determine which of several cross-hybridizing genes encodes the abundantly expressed mRNA found in the desired tissue. For example, tests indicate that pZ130 (see Example 4) is a member of a small gene family however, the pZ7 probe is capable of distinguishing pZ130 from the remainder of the family members.

The cDNA obtained as described can be sequenced to determine the open reading frame (probable protein-coding region) and the direction of transcription so that a desired target DNA sequence can be later inserted at the correct site and in the correct orientation into a transcription cassette. Sequence information for the cDNA clone also facilitates characterization of corresponding genomic clones including mapping and subcloning as described below. At the same time, a genomic library can be screened for clones containing the complete gene sequence including the control region flanking the transcribed sequences. Genomic clones generally contain large segments of DNA (approximately 10-20 kb) and can be mapped using restriction enzymes, subcloned and partially sequenced to determine which segments contain the developmentally regulated gene.

Using the restriction enzyme map and sequence information, plasmids can be designed and constructed which have the putative ovary gene or other desired promoter regions attached to genes which are to be expressed in ovary and/or other desired tissue. These hybrid constructions are tested for their pattern of expression in transformed, regenerated plants to be sure that the desired timing and/or tissue expression and/or the overall level of expression has been maintained successfully when the promoter is no longer associated with the native open reading frame. Using the method described above, several transcriptional regulatory regions have been identified. One example is the tomato-derived transcriptional initiation region which regulates the expression of the sequence corresponding to the pZ130 cDNA clone. Sequences hybridizable to the pZ130 clone, for example, probe pZ7, show abundant mRNA, especially at the early stages of anthesis. The message is expressed in ovary integument and ovary outer pericarp tissue and is not expressed, or at least is not readily detectable, in other tissues or at any other stage of fruit development. Thus, the pZ130 transcriptional initiation region is considered ovary-specific for purposes of this invention. FIG. 1 provides the DNA sequence of cDNA clone pZ130. The native function of the amino acid sequence encoded by the structural gene comprising pZ130 is unknown.

A second example is an ovary tissue transcription initiation control region derived from tomato which shows abundant mRNA in ovaries prepared from unopened flowers, no detectable mRNA in ripening fruit, but, unexpectedly, shows increased mRNA in response to tomato leaf wounding. Sequences hybridizable to the pZ70 clone, for example probe pZ8, show a high level of expression and tissue selectivity in ovary tissue. When preanthesis tomato ovaries are hybridized to sense and anti-sense RNA sequences, the anti-sense probe hybridizes specifically to the inner core region of the ovary and the outer region of the ovules (the integuments). As a result of the increased expression in response to leaf-wounding, the transcriptional initiation region of pZ70 may also find application as a wound-inducible promoter. The native activity of the amino acid sequence encoded by the pZ70 structural gene in the tomato ovary is unknown, but in the leaves, the metallocarboxypeptidase inhibitor protein may act as a natural insect tolerant agent. (See co-pending U.S. patent application Ser. No. 364,362, filed Jun. 9, 1989, entitled "Novel Pest Tolerance Gene and Method of Use" which disclosure is hereby incorporated by reference).

The remaining components of the transcriptional cassette are as follows. Downstream from, and under the regulatory control of, the ovary tissue transcriptional/translational initiation control region is a DNA sequence of interest which provides for modification of the phenotype of the structures maturing from ovary tissue, such as fruit. The DNA sequence may be any open reading frame encoding a peptide of interest, for example, an enzyme, or a sequence complementary to a genomic sequence, where the genomic sequence may be an open reading frame, an intron, a noncoding leader sequence, or any other sequence where the complementary sequence inhibits transcription, messenger RNA processing, for example, splicing, or translation. Such phenotypic modification can be achieved by modulating the production either of an endogenous product, for example as to the amount, relative distribution, or the like, or an exogenous expression product, for example to provide for a novel function or products therein. Of particular interest are DNA sequences encoding expression products associated with the development of plant fruit, including genes involved in metabolism of cytokinins, auxins, ethylene, abscisic acid, and the like. Methods and compositions for modulating cytokinin expression are described in co-pending U.S. Ser. No. 382,802, filed on Jul. 19, 1989, now abandoned, which disclosure is hereby incorporated by reference Alternatively, various genes, from other sources including other eukaryotic or prokaryotic sources, including bacteria, such as those from *Agrobacterium tumefaciens* T-DNA auxin and cytokinin biosynthetic gene products, for example, and mammals, for example interferons, may be used.

An expression cassette also comprises a transcriptional and translation termination region. The termination region which is employed will be primarily one of convenience, since the termination regions appear to be relatively interchangeable. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. In some embodiments, it may be desired to use the 3' termination region native to the ovary tissue transcription initiation region.

Depending upon the manner of introduction of the transcription cassette into the plant, other DNA sequences may be required For example, when using the Ti- or Ri-plasmid for transformation of plant cells, as described below, at least the right border and frequently both the right and left borders of the T-DNA of the Ti- or Ri-plasmids will be joined as flanking regions to the transcription construct. The use of T-DNA for transformation of plant cells has received extensive study and is amply described in EPA Ser. No. 120,516, Hoekema, In: The Binary Plant Vector System Offset-drukkerij Kanters B. V., Alblasserdam, 1985, Chapter V, Knauf, et al., Genetic Analysis of Host Range Expression by Agrobacterium, In: Molecular Genetics of the Bacteria-Plant Interaction, Puhler, A. ed.. Springer-Verlag, N.Y. 1983, p. 245, and An, et al., *EMBO J.* (1985) 4:277–284.

Alternatively, to enhance integration into the plant genome, terminal repeats of transposons may be used as borders in conjunction with a transposase. In this situation, expression of the transposase should be inducible, so that once the transcription construct is integrated into the genome, it should be relatively stably integrated.

The various constructs will normally be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed cells as compared to cells lacking the DNA which has been introduced. Components of DNA constructs including transcription cassettes of this invention may be prepared from sequences which are native (endogenous) or foreign (exogenous) to the host. By foreign is intended that the sequence is not found in the wild-type host into which the construct is introduced. Heterologous constructs will contain at least one region which is derived from a different gene than that from which the ovary tissue transcription initiation region is derived. The DNA sequences of this invention may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest.

In preparing the transcriptional cassettes, the various DNA fragments may be manipulated, so as to provide for DNA sequences in the proper orientation and, as appropriate, in proper reading frame for expression. Toward this end, adapters or linkers may be employed for joining the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved. Conveniently, the cassette may include a multiple cloning site downstream from the ovary-related transcription initiation region, so that the construct may be employed for a variety of sequences in an efficient manner.

By appropriate manipulations, such as restriction, chewing back or filling in overhangs to provide blunt ends, ligation of linkers, or the like, complementary ends of the fragments can be provided for joining and ligation.

In carrying out the various steps, cloning is employed, so as to amplify the amount of DNA and to allow for analyzing the DNA to ensure that the operations have occurred in proper manner. A wide variety of cloning vectors are available, where the cloning vector includes a replication system functional in *E. coli* and a marker which allows for selection of the transformed cell. Illustrative vectors include pBR332, pUC series, M13mp series, pACYC184, etc. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence. Each of the partial constructs may be cloned in the same or different plasmids.

A variety of techniques are available and known to those skilled in the art for introduction of the transcription cassette into a plant cell host. These techniques include transformation with DNA employing *A. tumefaciens* or *A. rhizogenes* as the transforming agent, protoplast fusion, injection, electroporation, particle accelerating, etc. For transformation with *Agrobacterium*, plasmids can be prepared in *E. coli* which contain DNA homologous with the Ti-plasmid, particularly T-DNA. The plasmid may or may not be capable of replication in Agrobacterium, that is, it may or may not have a broad spectrum prokaryotic replication system such as does, for example, pRK290, depending in part upon whether the transcription cassette is to be integrated into the Ti-plasmid or to be retained on an independent plasmid. The Agrobacterium host will contain a plasmid having the vir genes necessary for transfer of the T-DNA to the plant cell and may or may not have the complete T-DNA. For infection, particle acceleration and electroporation, disarmed Ti-plasmid lacking particularly the tumor genes found in the T-DNA region) may be introduced into the plant cell. By means of a helper plasmid, the transcription construct may be transferred to the *A. tumefaciens* and the resulting transformed organism used for transforming plant cells; explants may be cultivated with transformed *A. tumefaciens* or *A. rhizogenes* to allow for transfer of the transcription cassette to the plant cells. The plant cells are then placed in an appropriate selective medium for selection of transgenic cells which are then grown to callus, shoots grown and plantlets generated from the shoot by growing in rooting medium.

The cassettes of the subject invention may be employed for varying the phenotype of fruit. Transcriptional cassettes may be used when the transcription of an anti-sense sequence is desired. When the expression of a polypeptide is desired, expression cassettes providing for transcription and translation of the DNA sequence of interest will be used. Various changes are of interest; these changes may include modulation (increase or decrease) of formation of particular saccharides, hormones, enzymes, or other biological parameters. These also include modifying the composition of the final fruit, that is changing the ratio and/or amounts of water, solids, fiber or sugars.

Other phenotypic properties of interest for modification include response to stress, organisms, herbicides, brushing, growth regulator, and the like. These results can be achieved by providing for reduction of expression of one or more endogenous products, particularly an enzyme or cofactor, by producing a transcription product which is complementary (anti-sense) to the transcription product of a native gene, so as to inhibit the maturation and/or expression of the transcription product, or providing for expression of a gene, either endogenous or exogenous, to be associated with the development of a plant fruit.

The various sequences provided herein may be used as molecular probes for the isolation of other sequences which may be useful in the present invention, for example, to obtain related transcriptional initiation regions from the same or different plant sources. Related transcriptional initiation regions obtainable from the sequences provided in this invention will show at least about 60% homology, and more preferred regions will demonstrate an even greater percentage of homology with the probes. Of particular importance is the ability to obtain related transcription initiation control regions having the timing and tissue parameters described herein. For example, using the probe pZ130, at least 7 additional clones, have been identified, but not further characterized. Thus, by employing the techniques described in this application, and other techniques known in the art (such as Maniatis, et al., *Molecular Cloning; A Laboratory Manual* (Cold Spring Harbor, N.Y.) 1982), other transcription initiation regions capable of directing ovary tissue transcription as described in this invention may be determined. The constructs can also be used in conjunction with plant regeneration systems to obtain plant cells and plants; the constructs may also be used to modify the phenotype of a fruit and fruits produced thereby.

The following examples are offered by way of illustration and not by limitation.

EXPERIMENTAL

The following deposits have been made at the American Type Culture Collection (ATCC) (12301 Parklawn Drive, Rockville, Md. 20852). Bacteriophage Calgene Lambda 116 and Calgene Lambda 140, each containing a transcription initiation region of this invention, were deposited on Jul. 13, 1989 and were given accession numbers 40632 and 40631, respectively.

EXAMPLE 1

Construction of Pre-Anthesis Tomato Ovary cDNA Banks and Screening for Ovary-Specific Clones cDNA Library Preparation Tomato plants (*Lycopersicon esculentum* cv UC82B) were grown under greenhouse conditions. Poly(A)+-RNA was isolated as described by Mansson et al., *Mol. Gen. Genet.* (1985) 200:356-361. The synthesis of cDNA from poly(A)+RNA, prepared from ovaries of unopened tomato flowers (pre-anthesis stage), was carried out using the BRL cDNA Cloning Kit following the manufacturer's instructions (BRL; Bethesda, Md.). Addition of restriction endonuclease EcoRI linkers (1078, New England Biolabs; Beverly, Mass.) to the resulting double-stranded cDNA was accomplished by using the procedures described in Chapter 2 of *DNA Cloning Vol. I: A Practical Approach*, Glover, ed., (IRL Press, Oxford 1985). Cloning the cDNA into the EcoRI site of the phage Lambda ZAP (Stratagene; La Jolla, Calif.) and packaging the resulting recombinant phage (using Giga-Pack Gold, Stratagene) was carried out as described in the respective commercial protocols.

Two cDNA libraries were prepared as described above from the same pre-anthesis stage mRNA. For the second library, which contained significantly longer cDNA than the first, the poly(A)+RNA sample was run through an RNA spin column (Boehringer Mannheim Biochemicals; Indianapolis, Ind.), following the manufacturer's directions, prior to the cloning procedures.

cDNA Library Screening

The first cDNA library was screened by differential hybridization using 32P-labelled cDNA probes made from pre-anthesis mRNA, leaf mRNA and young seedling mRNA. Clones were selected based on hybridization to only pre-anthesis mRNA. The cDNAs corresponding to the selected Lambda ZAP (Stratagene) clones were excised from the phage vector and propagated as plasmids (following the manufacturer's instructions).

From an initial screen of 1000 cDNAs, 30 selected clones falling into five classes based on the sequences of their cDNA inserts were isolated. Two clones, clones pZ7 and pZ8, were selected for further study. The DNA sequences of pZ7 and pZ8 are shown as the underlined portions of FIGS. 1 and 4, respectively.

Several thousand recombinant clones from the second cDNA library were screened by plaque hybridization (as described in the Stratagene Cloning Kit Instruction Manual) with a mixture of radiolabelled DNA probes. Screening of approximately three thousand recombinant clones from the second library with the pZ7 and pZ8 DNA probes yielded selection of fourteen clones which had intense hybridization signals. The clones selected were excised from the phage vector and propagated as plasmids. DNA was isolated from each clone, cut with the restriction endonuclease EcoRI, then electrophoresed through a 0.7% agarose gel. Duplicate blot hybridizations were performed as described in Maniatis et al., *Molecular Cloning: A Laboratory Manual* (Cold Spring Harbor, N.Y., 1982) with radiolabelled probes representing the genes of interest (pZ7 and pZ8). Seven clones which hybridized to pZ7 and three clones which hybridized to pZ8 were selected. The longest of these for each probe, pZ130 (pZ7-hybridizing) and pZ70 (pZ8-hybridizing), were characterized further and used in additional experiments.

EXAMPLE 2

Analysis of cDNA Clones Northern Analysis

Tissue-specificity of the cDNA clones was demonstrated as follows: RNA was isolated from 1, 2, 3, 4, 5, 6, 7, 10, 14, 17 and 21 day post-anthesis, anthesis and pre-anthesis stage tomato ovaries, tomato leaves and unorganized tomato callus using the method of Ecker and Davis, *Proc. Natl. Acad. Sci. USA*, 84:5203 (1987) with the following modifications. After the first precipitation of the nucleic acid, the pellets were resuspended in 2 ml of diethylpyrocarbonate (DEP)-treated water on ice. The solutions were brought to 1 mM $MgCl_2$ and ¼ volume of 8M LiCl was added. The samples were mixed well and stored at 4° C. overnight. The samples were then centrifuged at 8,000 RPM for 20 min. at 4° C. The pellets were dried, resuspended in DEP-treated water on ice as before and ethanol-precipitated once more. The RNAs were electrophoresed on formaldehyde/agarose gels according to the method described by Fourney et al., *Focus* (1988) 10:5–7, immobilized on Nytran membranes (Schleicher & Schuell; Keene, NH) and hybridized with $^{32}$P-labelled probes.

Based upon the Northern analysis with a $^{32}$P-labelled pZ7 EcoRI insert DNA or a pZ8 EcoRI insert DNA, it is clear that both of these genes are most highly expressed at anthesis in tomato variety UC82B and somewhat less highly expressed prior to and a day following the opening of the flower. FIG. 6 shows tomato flowers at various stages of development and immediately below, a representative ovary dissected from a flower at the same stage of development. As seen in FIG. 6, by two days after the onset of anthesis, the expression of both genes had dropped off dramatically. The size of the mRNA species hybridizing to the pZ7 probe was approximately 800 nt and to the pZ8 probe approximately 500 nt.

From two days post-anthesis, pZ8 RNA accumulation was apparently maintained at a relatively low level while pZ7 RNA accumulation continued to drop off steadily until, by three weeks post-anthesis, it was undetectable by this analysis. pZ8 RNA accumulation was not detectable by the method described above in RNA samples isolated from tomato fruit older than the immature green stage of fruit ripening. No RNA hybridizing to pZ7 or pZ8 was found in callus tissue; no RNA hybridizing to pZ7 was found in leaf tissue; on longer exposures a barely detectable hybridization signal for pZ8 was seen in leaf RNA.

Expression Level

Message abundance corresponding to the cDNA probes was determined by comparing the hybridization intensity of a known amount of RNA synthesized in vitro from the clones (using T7 or T3 RNA polymerase in the Riboprobe System (Promega)) to RNA from anthesis stage and three week old tomato ovaries. This analysis indicated that pZ7 and pZ8 cDNAs represent abundant RNA classes in anthesis-stage tomato ovaries, being approximately 5% and 2% of the message, respectively.

Cellular Specificity

The cellular specificity of the cDNA probes may be demonstrated using the technique of in situ hybridization. Preanthesis stage UC82B tomato ovaries were fixed overnight in a 4% paraformaldehyde, phosphate buffered saline (PBS), 5 mM $MgCl_2$ solution, pH 7.4 (PBS is 10 mM phosphate buffer, pH 7.4, 150 mM NaCl) (Singer et al., *Biotechniques* (1986) 4:230–250). After fixation, the tissue was passed through a graded tertiary butyl alcohol (TBA) series, starting at 50% alcohol, infiltrated with Paraplast and cast into paraffin blocks for sectioning (Berlyn and Miksche, *Botanical Microtechnique and Cytochemistry*, (1976) Iowa). Embedded ovaries were transversely cut, 8 μm thick sections, on a Reichert Histostat rotary microtome. Paraffin ribbons holding 5–7 ovary sections were affixed to gelatin-chrom alum subbed slides (Berlyn and Miksche (1976) supra) and held in a dust-free box until in situ hybridizations were performed. Slides ready to be hybridized were deparaffinized in xylene and rehydrated by passing through an ethanol hydration series as described in Singer et al., supra (1986).

A 2X hybridization mix was made consisting of 100 μl 20X SSC, 20 μl 10% BSA, 100 μl 750 mM DTT, 200 μl 50% dextran sulfate, 50 μl RNasin, and 30 μl sterile water. Sense and antisense $^{35}$S-RNA probes were generated from cDNAs of interest using T3 and T7 RNA polymerases in in vitro transcription (Riboprobe Promega Biotec or Stratagene) reactions following the manufacturer's protocol. 2.5 μl tRNA (20 mg/ml), 2.5 μl salmon sperm DNA (10 mg per ml) and $4 \times 10^6$ cpm/probe were dried down using a lyophilizer. This mix was then resuspended in 25 μl 90% formamide containing 25 μl 2X hybridization mix per slide. 40 μl of this hybridization mix was placed on each slide. A cover slip was placed over the sections and edges sealed with rubber cement. Slides were placed in slide holders inside a glass slide box, covered, and placed in a 37° C. dry oven overnight to hybridize. Posthybridization treatments were as described in Singer et al., (1986), supra.

Autoradiography was performed as described in *KODAK Materials for Light Microscope* (KODAK (1986); Rochester, N.Y.) using liquid emulsion NTB-3. Slides are left to expose in a light-tight box for approximately two weeks. After developing the autoradiographic slides, sections were stained in 0.05% toluidine blue and then dehydrated through a graded alcohol series; xylene:100% ethanol, 1:1, followed by 2 changes of 100% xylene, five minutes in each solution. Coverslips were mounted with Cytoseal (VWR; San Francisco, Calif.) and left on a slide warmer until dry (45°-50° C., 1-2 days). Autoradiographic slides were then ready for microscopic examination.

When pre-anthesis tomato ovaries were hybridized to sense and antisense $^{35}$S-pZ7 RNA, the antisense transcripts hybridized specifically to the outer pericarp region of the ovary and to the outer region of the ovules (the integuments). The sense transcripts (negative control) showed no hybridization. When preanthesis tomato ovaries were hybridized to sense and antisense $^{35}$S-pZ8 RNA, the antisense transcript hybridized specifically to the inner core region of the ovary and to the outer region of the ovules. The sense transcripts showed no hybridization.

In summary, the mRNA transcripts encoded by the genes corresponding to pZ7 and pZ8 were abundantly expressed during a very specific stage of tomato fruit development, primarily at anthesis and at a day prior to and after the opening of the flower. The transcripts additionally were expressed in a specific subset of tomato ovary cell types during that stage of development particularly in the integuments (pZ7 and pZ8) as well as the ovarian outer pericarp (pZ7) and inner core region (pZ8).

EXAMPLE 3

Sequencing of pZ130 and pZ70 cDNA Clones

The complete DNA sequences of the cDNA pZ130 and pZ70 clones were determined using the Sanger et al. (1971) dideoxy technique. The DNA sequences of both pZ130 and pZ70 were translated in three frames. The sequences, including the longest open reading frame for each, are shown in FIG. 1 (pZ130) and FIG. 4 (pZ70).

EXAMPLE 4

Analysis of Gene Family

Southern analysis was performed as described by Maniatis et al., supra, (1982). Total tomato DNA from cultivar UC82B was digested with BamHI, EcoRI and HindIII, separated by agarose gel electrophoresis and transferred to nitrocellulose. Southern hybridization was performed using $^{32}$P-labelled probes produced by random priming of pZ130 or pZ70. A simple hybridization pattern indicated that the genes encoding pZ130 and pZ70 are present in a few or perhaps only one copy in the tomato genome.

Additional analysis, using a pZ130 hybridization probe to hybridize to tomato genomic DNA digested with the restriction endonuclease BglII, indicated that this gene is actually a member of a small (approximately 5–7 member) family of genes. The original pZ7 cDNA clone, consisting of sequences restricted to the 3'-untranslated region of the longer pZ130 clone, however, hybridizes intensely only to one band and perhaps faintly to a second band based on Southern analysis using BglII digested tomato genomic DNA.

EXAMPLE 5

Preparation of a pZ130 Expression Construct
Preparation of Genomic Clones

Two genomic clones, one representing each of cDNA clones pZ130 and pZ70, were obtained as follows. A genomic library constructed from DNA of the tomato cultivar UC82B, partially digested with the restriction endonuclease Sau3A, was established in the lambda phage vector, lambda-FIX according to the manufacturer's instructions (Stratagene; La Jolla, Calif.). This library was screened using $^{32}$P-labelled pZ130 and pZ70 as probes. A genomic clone containing approximately 14.5 kb of sequence from the tomato genome which hybridized to pZ70 was isolated. The region which hybridizes to the pZ70 probe was found within the approximately 2 kb XbaI-HindIII restriction fragment of Calgene Lambda 116 (See FIG. 5). A second genomic clone, containing approximately 13 kb of sequence from the tomato genome and hybridizing to pZ130 (and pZ7) was isolated. The region which hybridized to the pZ130 probe was found within the larger EcoRI-HindIII restriction fragment of Calgene Lambda 140 (See FIG. 3).

Preparation of pCGN2015 pCGN2015 was prepared by digesting pCGN565 with HhaI, blunting with mung bean nuclease, and inserting the resulting fragment into an EcoRV digested BluescriptKSM13-(Stratagene) vector to create pCGN2008. pCGN2008 was digested with EcoRI and HindIII, blunted with Klenow, and the 1156 bp chloramphenicol fragment isolated. BluescriptKSM13+(-Stratagene) was digested with DraI and the 2273 bp fragment isolated and ligated with the pCGN2008 chloramphenicol fragment creating pCGN2015.

Preparation of pCGN2901/pCGN2902 pCGN2901 contains the region surrounding the pZ7-hybridizing region of the pZ130 genomic clone, including approximately 1.8 kb in the 5' direction and approximately 4 kb in the 3'-direction. To prepare pCGN2901, Calgene Lambda 140 was digested with SalI and the resulting fragment which contains the pZ7-hybridizing region was inserted into pCGN2015, at the pCGN2015 unique SalI site, to create pCGN2901.

pCGN2902 contains the other SalI fragment (non-pZ7-hybridizing) of the pZ130 genome derived from SalI digestion of Calgene Lambda 140, also put into a pCGN2015 construct.

Preparation of a pZ130 Expression Construct

Plasmid DNA isolated from pCGN2901 was digested to completion with NcoI and then treated with exonuclease isolated from mung bean (Promega, Madison, Wis.) to eliminate single-stranded DNA sequences including the ATG sequence making up a portion of the NcoI recognition sequence. The sample was then digested to completion with SacI. The resulting 1.8 kb (approximate) 5' SacI to NcoI fragment was then inserted into a pUC-derived ampicillin-resistant plasmid, pCGP261 (described below), that had been prepared as follows. pCG261 was digested to completion with XbaI, the single-stranded DNA sequences were filled in by treatment with the Klenow fragment of DNA polymerase I, and the pCGP261 DNA redigested with SacI. The resulting expression construct contained, in the 5' to 3' direction of transcription, an ovary tissue promoter derived from Lambda 140, a tmr gene and tmr 3'-transcriptional termination region.

The plasmid pCGP261 contains the sequences from position 8,762 through 9,836 from the *Agrobacterium tumefaciens* octopine Ti plasmid pTi15955 (as sequenced by Barker et al, *Plant Molec. Biol.* (1983) 2:335–350). This region contains the entire coding region for the genetic locus designated tmr which encodes isopentenyltransferase (Akiyoshi et al., PNAS (1984) 81:4776-4780), 8 bp 5' of the translation initiation ATG codon and 341 bp of sequences 3' to the translation stop TAG codon.

Plasmid pCGP261 was created as follows. Plasmid pCGN1278 (described in co-pending application U.S. Ser. No. 382,176, filed Jul. 19, 1989, which is hereby incorporated in its entirety by reference) was digested with XbaI and EcoRI. The single-stranded DNA sequences produced were filled in by treatment with the Klenow fragment of DNA polymerase I. The XbaI to EcoRI fragment containing the tmr gene was then ligated into the vector m13 Bluescript minus (Stratagene Inc., La Jolla, Calif.) at the SmaI site, resulting in plasmid pCGP259. All of the region found upstream of the ATG translation initiation codon and some of the tmr gene coding region was eliminated by digesting pCGP259 with BspMI and BstXI. The resulting coding region and 8 bp of the sequence originally found upstream of the first ATG codon was reintroduced into the plasmid and an XbaI site introduced into the plasmid via a synthetic oligonucleotide comprising the following sequence: 5' AATTAGATGCAGGT-CCATAAGTTTTTTCTAGACGCG 3'. The resulting plasmid is pCGP261. An XbaI to KpnI fragment of pCGP261 containing the pZ130 gene 5' and tmr gene coding and 3' region construct was then inserted into a binary cassette such as pCGN1557 and transgenic plants prepared. (See co-pending application U.S. Ser. No. 382,176 described above).

EXAMPLE 6 pZ130 Promoter Cassette

The pZ130 cassette contains 1.8 kb of DNA 5' of the translational start site and the 3' region (from the TAA stop codon to a site 1.2 kb downstream) of the pZ130 gene. The pZ130 cassette was constructed as follows.

Transcriptional Initiation Region

Plasmid DNA isolated from pCGN2901 (see above) was digested to completion with NcoI and then treated with exonuclease isolated from mung bean (Promega, Madison, Wis.) to eliminate single-stranded DNA sequences, including the ATG sequence making up a portion of the NcoI recognition sequence. The sample was then digested to completion with SacI. The resulting 1.8 kb 5' SacI to NcoI fragment was then inserted into pCGN2015 (described above) to create pCGN2904.

In order to eliminate redundant restriction enzyme sites and make subsequent cloning easier, plasmid DNA isolated from pCGN2904 was digested to completion with SalI and EcoRI and the resulting 1.8 kb fragment, containing the pZ130 5' sequences, inserted into pBluescriptII (Stratagene; La Jolla, Calif.) to create pCGN2907.

Transcriptional and Translational Termination Region

Plasmid DNA isolated from pCGN2901 was digested to completion with EcoRI and BamHI. The resulting 0.72 kb EcoRI to BamHI fragment located downstream (3') from the pZ130 coding region was inserted into pCGN2907 creating pCGN2908.

The insertion of the 0.5 kb (approximately) DNA sequence, including the pZ130 gene TAA stop codon and those sequences between the stop codon and the EcoRI site downstream (3') and the addition of unique restriction sites to facilitate insertion of foreign genes, was accomplished as follows.

A polylinker/"primer" comprising the sequence 5'-GTTCCTGCAGCATGCCCGGGATC-GATAATAATTAAGTGAGGC-3' was synthesized to create a polylinker with the following sites: PstI-SphI-SmaI-ClaI and to include the pZ130 gene TAA stop codon and the following (3') 13 base pairs of the pZ130 gene 3' region sequence. Another oligonucleotide comprising the sequence 5'- CAAGAATT-CATAATATTATATAC 3' was synthesized to create a "primer" with an EcoRI restriction site and 16 base pairs of the pZ130 gene 3'-region immediately adjacent to the EcoRI site located approximately 0.5 kb 3' of the pZ130 gene TAA stop codon.

These synthetic oligonucleotides were used in a polymerase chain reaction (PCR) in which plasmid DNA isolated from pCGN2901 was used as the substrate in a thermal cycler (Perkin-Elmer/Cetus, Norwalk, Conn.) as per the manufacturer's instructions. The resulting 0.5 kb DNA product was digested to completion with PstI and EcoRI and the resulting 0.5 kb DNA fragment inserted into pCGN2908 to create pCGN2909. The complete DNA sequence of the 0.5 kb region from the PstI site to the EcoRI site was determined using the Sanger et al. (1971) dideoxy technique to verify that no mistakes in the sequence had occurred between the oligonucleotide primers during the PCR reaction.

The pZ130 cassette, pCGN2909, thus comprises the 5' pZ130 DNA sequences from the SalI site at position 808 to position 2636 (see FIG. 2), unique PstI, SphI and SmaI sites which can be conveniently used to insert genes, and the 3' pZ130 DNA sequences from the TAA stop codon at position 3173 (FIG. 2) through the BamHI site at position 4380.

EXAMPLE 7

Preparation and Analysis of Test Constructs

A β-glucuronidase (GUS) reporter gene was used to evaluate the expression and tissue specificity of the pZ130-GUS constructions. GUS is a useful reporter gene in plant systems because it produces a highly stable enzyme, there is little or no background (endogenous) enzyme activity in plant tissues, and the enzyme is easily assayed using fluorescent or spectrophotometric substrates. (See, for example, Jefferson, *Plant Mol. Rep.* (1987) 5:387-405.) Histochemical stains for GUS enzyme activity are also available which can be used to analyze the pattern of enzyme accumulation in transgenic plants. Jefferson (1987), supra.

Preparation of Test Constructs pCGN2917 and pCGN2918

These constructs contain 1.8 kb of pZ130 5' sequence, the GUS gene encoding region and 1.2 kb of pZ130 3' sequence. They differ from each other only in the orientation of the pZ130/GUS construction with respect to the other elements of the binary vector plasmid for example, the 35S promoter from CaMV.

The constructs were made by inserting the PstI fragment of pRAJ250 (Jefferson, (1987) supra), or any other plasmid construct having the PstI fragment containing the GUS coding region, into the PstI site of pCGN2909. The resulting plasmid, having the GUS gene in the sense orientation with respect to the pZ130 gene promoter region, was named pCGN2914. The pZ130/GUS construction was excised as an XbaI to Kpn fragment and cloned into the binary vectors pCGN1557 and pCGN1558 to make pCGN2917 and pCGN2918, respectively. pCGN1557 and pCGN1558 are described in McBride and Summerfelt, *Plant Mol. Bio.* (1990) 14:269-296.

Analysis of GUS Enzyme Activity

β-glucuronidase activity of transformants was measured using 4-methyl-umbelliferyl glucuronide as substrate, as outlined in Jefferson (1987) supra. GUS enzyme activity was easily detected in the ovaries of the transformed plants and quantitatively was quite high in comparison with the activity background observed in ovaries isolated from nontransformed tomato plants and from leaves of transformed plants. Interestingly, upon comparison of the pCGN2917 and pCGNZ918 transformants, it was found that proximity to a 35S CaMV enhancer region (pCGN1558) may reduce, or eliminate, ovary-tissue specificity.

All publications and patent applications cited in this specification are herein incorporated by reference as if each individual publication or patent application were specifically and individually indicated to be incorporated by reference.

Although the foregoing invention has been described in some detail, by way of illustration and example for purposes of clarity and understanding, it will be readily apparent to those of ordinary skill in the art that certain changes and modifications may be made thereto, without departing from the spirit or scope of the appended claims.

What is claimed is:

1. A DNA transcription construct comprising a tomato pZ130 transcriptional initiation region joined in the direction of transcription to a heterologous DNA sequence of interest under the regulatory control of said initiation region.

2. The construct of claim 1 further comprising a selectable marker.

3. A cell comprising: the construct of claim 1.

4. A plant cell comprising the DNA construct of claim 1.

5. A plant comprising:
   plant cells comprising a DNA transcription construct in the genome of said cells, said construct comprising
   a tomato pZ130 transcriptional initiation region joined in the direction of transcription to a DNA sequence of interest under the regulatory control of said initiation region, and a transcriptional termination region,
   wherein said DNA sequence of interest is heterologous to at least one of said transcriptional initiation and termination regions.

6. The plant according to claim 5, wherein said plant is a tomato plant.

7. A method for producing a polypeptide of interest in tomato ovary tissue, said method comprising:
   growing a tomato plant to produce fruit, wherein cells of said fruit comprise in their genome a transcription construct comprising a tomato pZ130 transcriptional initiation region joined in the direction of transcription to a DNA sequence of interest under the regulatory control of siad initiation region, said construct further comprising a transcriptional termination region,
   wherein said DNA sequence of interest is heterologous to at least one of said transcriptional initiation and termination regions, and wherein said DNA sequence of interest encodes said polypeptide of interest.

8. The method according to claim 7, wherein said transcription construct further comprises at least one DNA sequence encoding a means for selection.

* * * * *